(12) United States Patent
Sakurai et al.

(10) Patent No.: US 7,981,267 B2
(45) Date of Patent: Jul. 19, 2011

(54) CAPILLARY ELECTROPHORESIS DEVICE

(75) Inventors: Toshiyuki Sakurai, Honjo (JP); Takeshi Ohura, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 123 days.

(21) Appl. No.: 12/352,954

(22) Filed: Jan. 13, 2009

(65) Prior Publication Data
US 2009/0200169 A1 Aug. 13, 2009

(30) Foreign Application Priority Data
Feb. 13, 2008 (JP) .................................. 2008-031275

(51) Int. Cl.
*G01N 27/453* (2006.01)
(52) U.S. Cl. ........................................ 204/601; 204/604
(58) Field of Classification Search .......... 204/451–455, 204/601–605; 422/99, 100
See application file for complete search history.

(56) References Cited

U.S. PATENT DOCUMENTS
2003/0221965 A1 * 12/2003 Seino et al. ................... 204/603

FOREIGN PATENT DOCUMENTS
JP 2006-276039 10/2006

* cited by examiner

*Primary Examiner* — Alex Noguerola
(74) *Attorney, Agent, or Firm* — McDermott Will & Emery LLP

(57) ABSTRACT

An object of the present invention is to prevent a variation in heat dissipating effect of a capillary between a holder part and an oven, to improve reproducibility of migration time, and to reduce a variation of migration time among capillaries in a single electrophoresis run. A cylindrical wall is formed in an upper part of a septa that covers a container holding a solution, and the cylindrical wall surrounds a capillary hole through which a capillary penetrates. Accordingly, the capillary is prevented from being directly affected by wind generated between the septa and the oven.

2 Claims, 7 Drawing Sheets

Wind circulating inside of chamber

CAPILLARY ELECTROPHORESIS DEVICE

CLAIM OF PRIORITY

The present application claims priority from Japanese application JP 2008-31275 filed on Feb. 13, 2008, the content of which is hereby incorporated by reference into this application.

BACKGROUND OF THE INVENTION

1. Field of the Invention

The present invention relates to a capillary electrophoresis device that separates and analyzes a sample, such as nucleic acid and protein, by electrophoresis.

2. Description of the Related Art

A solution, such as a sample, an assay, a buffer, or a rinse, which is used in a capillary electrophoresis device, is held in a container sealed by a septa. A capillary is filled with a separation medium, and the separation medium comes in contact with a liquid inside of the container through a hole formed in the septa. When a high voltage is applied to the capillary for carrying out electrophoresis, the separation medium filled inside of the capillary generates heat due to the generation of Joule heat, and the capability of separating a sample is decreased due to heat diffusion. Conventionally, in order to prevent the generation of heat in a separation medium and maintain a constant temperature of the separation medium, the capillary is put through inside of an oven having a temperature control mechanism. The technique is described in Japanese Unexamined Patent Application Publication No. 2006-276039.

SUMMARY OF THE INVENTION

Since a holder part that stores a solution, such as an assay, a buffer and a rinse, is attached to and detached from the capillary by the use of an auto sampler, the holder part is installed outside of the oven. Meanwhile, a region between the holder part and the oven is affected by wind circulating inside of the device by a cooling fan. Accordingly, it has been revealed that, when the temperature and the speed of the wind are not uniform, reproducibility of migration time is deteriorated, and a variation of migration time among multiple capillaries in a single electrophoresis run is increased.

An object of the present invention is to provide a capillary electrophoresis device in which a capillary between a holder part and an oven is not affected by air circulating inside of the device.

In the present invention, it is configured so that airflow circulating inside of a device may not directly blow onto a capillary electrode that is located outside of an oven. As an example, the present invention includes: a container that houses a sample or an electrolytic solution, and has an opening in an upper part thereof, and a septa having a capillary hole through which a capillary electrode projecting from a load header penetrates, the septa covering the upper part opening of the container. The septa has in an upper part thereof a structure that surrounds the capillary electrode so that air circulating inside of the device does not directly blow onto the capillary electrode.

According to the present invention, air circulating inside of the device does not directly blow onto the capillary (capillary electrode) on the side of a sample injection end; therefore, a variation of migration time among multiple capillaries and deterioration in reproducibility can be prevented.

DESCRIPTION OF THE PREFERRED EMBODIMENTS

Figure 1:
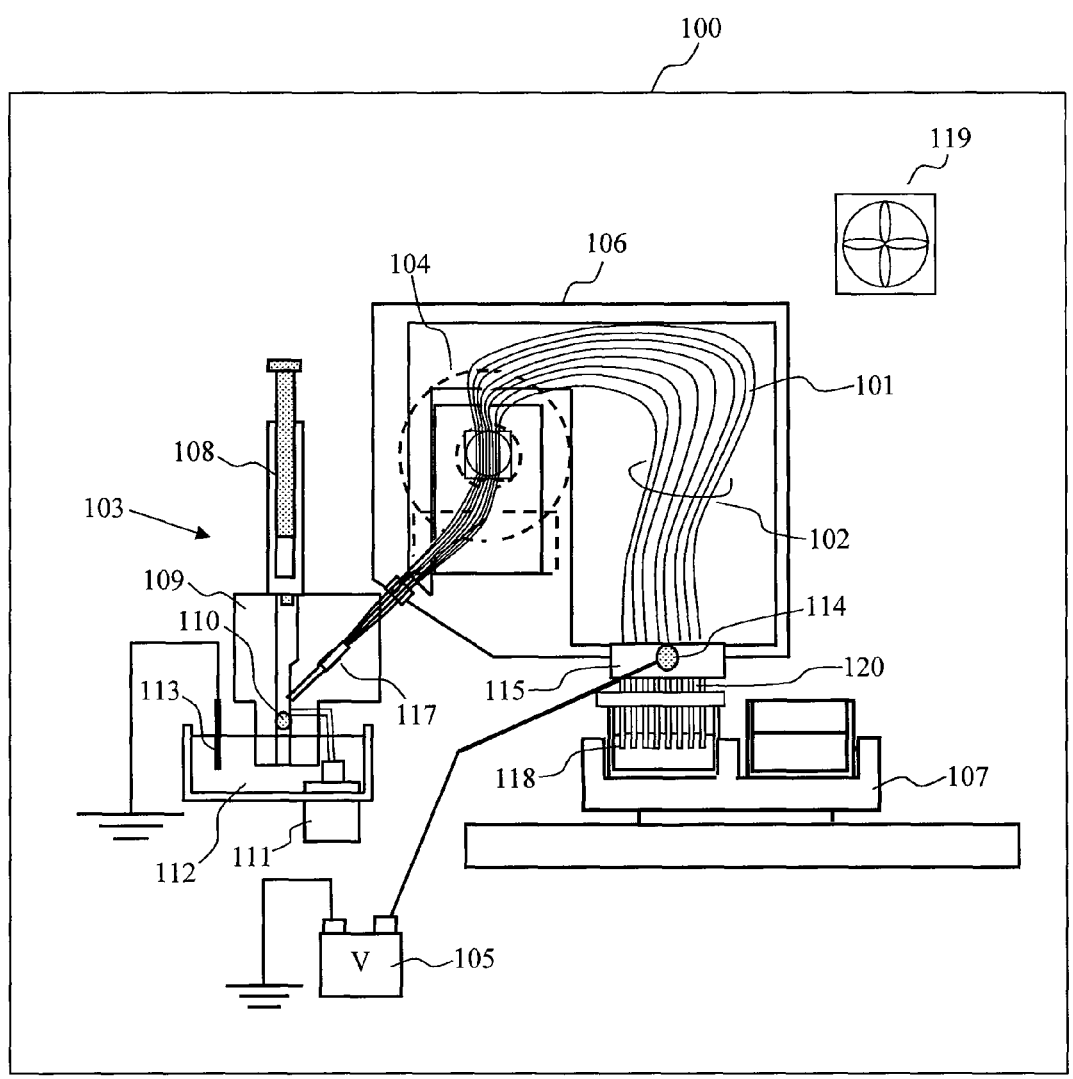
FIG. 1 is a schematic view of a capillary electrophoresis device.

FIG. 1 is a schematic view of a capillary electrophoresis device. A capillary electrophoresis device 100 includes: a capillary array 102 containing a single or multiple capillaries 101; a pump mechanism 103 for injection of a polymer to the capillary 101; a detector 104 that irradiates a sample inside of the capillary 101 with light and detects fluorescence from the sample; a high-voltage power supply 105 for applying a high voltage to the capillary 101; an oven 106 for maintaining a main part of the capillary 101 at a constant temperature; and an auto sampler 107 for transferring a container holding a sample, a solution, or the like.

The capillary 101 is an exchangeable member, and is exchanged when a different measurement technique is adopted or when damage or quality deterioration is observed in the capillary 101. The capillary 101 is composed of a glass tube having an inside diameter in a range from several tens to several hundreds of microns and an outside diameter of several hundreds of microns, and is coated on a surface thereof with polyimide. Inside of the capillary 101 is filled with a separation medium for causing migration time difference during electrophoresis. As for the separation medium, there are both a liquid medium and an illiquid medium, and a liquid polymer is used in the present example.

The capillary array 102 is provided at one end thereof with a capillary head 117 arranged and at the other end with a capillary cathode electrode 118 formed. The capillary head 117 is formed by putting an end part of the capillary array 102, and has a function to connect the pump mechanism 103 and the capillary array 102. The capillary cathode electrode 118 is in contact with a sample, a solution, and the like. On the side of the capillary cathode electrode 118, the capillary array 102 is fixed by a load header 115. The load header 115 has a cathode electrode 114 and a hollow capillary electrode 120 made of metal mounted thereto. There is continuity between the cathode electrode 114 and the capillary electrode 120. The capillary cathode electrode 118 penetrates through the capillary electrode 120 and projects from a tip thereof.

The detector 104 is composed of an irradiation system and a detection system. The irradiation system of the detector 104 has a function to irradiate a part in which a polyimide coating is removed in the capillary 101, that is a detection region, with an exciting light. The detection system has a function to detect fluorescence from a sample in the detection region of the capillary 101. A sample is analyzed by the light detected by the detection system.

The pump mechanism 103 is connected to: a syringe 108; a block 109; a check valve 110; a polymer container 111; and an anode buffer container 112. The capillary head 117 is connected to the block 109 so as to connect the capillary 101 and a flow path inside of the block 109. By operating the syringe 108, polymer inside of the polymer container 111 is filled or refilled into the capillary 101 through the flow path inside of the block 109. Refill of polymer inside of the capillary 101 is carried out for every measurement in order to improve measurement performance.

An anode electrode 113 is arranged in the anode buffer container 112. The high-voltage power supply 105 applies a high voltage between the anode electrode 113 and the cathode electrode 114. The oven 106 maintains the temperature of the capillary 101 constant by sandwiching the capillary array 102 in a planar manner with a temperature control board installed with a heat insulating material and a heater. A temperature sensor for feedback is attached to the temperature control board. Meanwhile, by fixing the load header 115 of the capillary array 102 to the oven 106, a tip of the capillary head 117 can be fixed at a desired position.

The auto sampler 107 includes three electric motors and a linear guide for moving a motion stage, and is capable of moving the motion stage in three axial directions of up and down, left and right, and front and back. The motion stage can transfer a buffer container, a rinse container, a waste container, and a sample plate to the capillary cathode electrode 118 if required. A cooling fan 119 circulates air inside of the device in order to prevent temperature rise by a heat-generating body, such as the high-voltage power supply 105.

Figure 2:
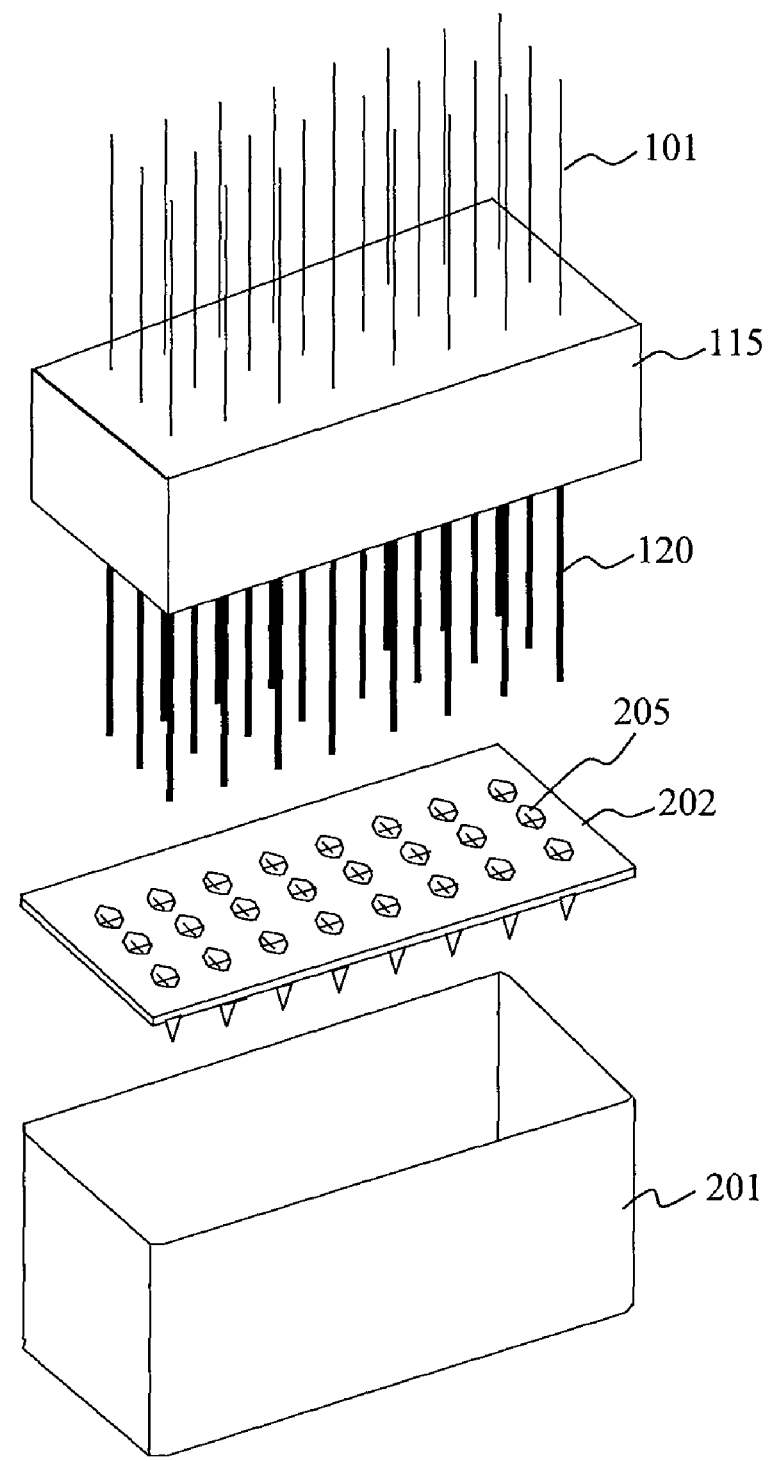
FIG. 2 is an explanatory view of a structure of a commonly-used holder part used in a capillary electrophoresis device.
Figure 3:
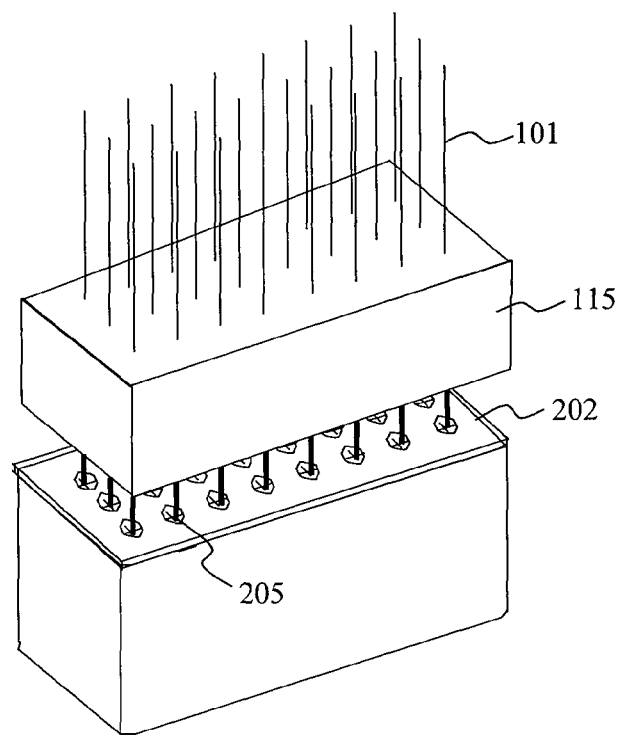
FIG. 3 is a view illustrating an assembly state of the holder part.

FIG. 2 is an exploded assembly view describing a structure of a commonly-used holder part used in a capillary electrophoresis device. The holder part includes: a container 201 for housing a solution; and a septa 202 having a capillary hole 205 through which the capillary 101 penetrates. FIG. 3 illustrates a state in which the holder part is assembled, and illustrates a state in which multiple capillaries 101 are respectively inserted into the capillary holes 205. An opening part of the container 201 is sealed by the septa 202 so as to prevent evaporation of the solution. The hollow capillary electrode 120 and the tip part of the capillary 101 mounted therein penetrates through the capillary hole 205 formed in the septa 202, and is inserted into the container 201 and dipped into a solution inside of the container 201.

Figure 4:
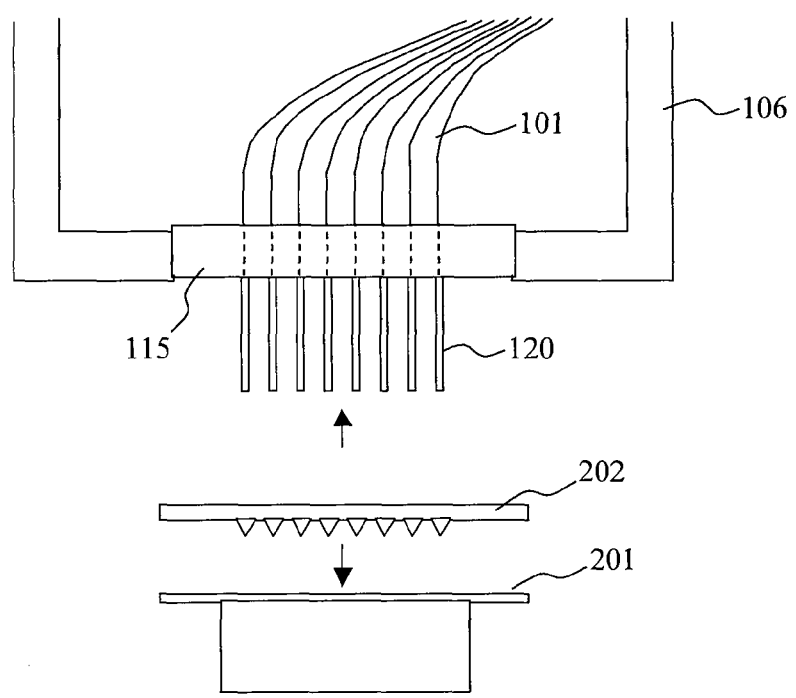
FIG. 4 is a view illustrating the relationship between a capillary electrode and a conventional holder part.
Figure 5:
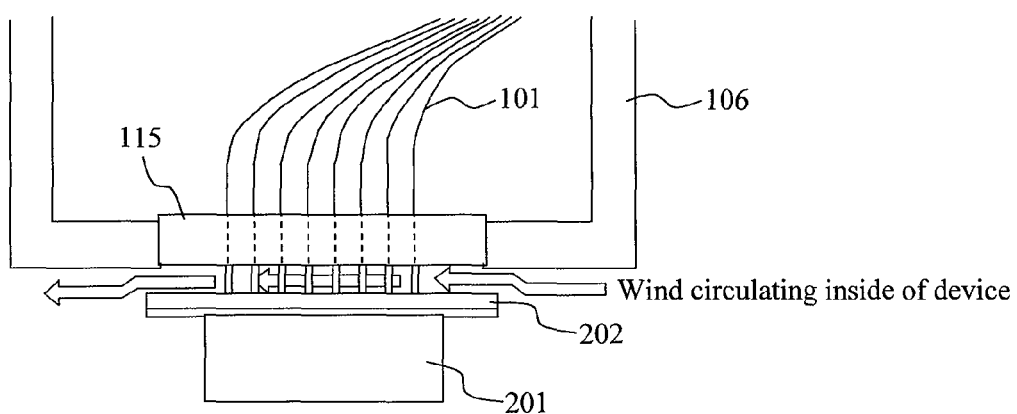
FIG. 5 is a view illustrating a state in which air circulating inside of the device goes by a capillary between the conventional holder part and an oven.

FIG. 4 and FIG. 5 are views describing a problem in a holder part of a conventional capillary electrophoresis device. FIG. 4 is a view illustrating the relationship among the hollow capillary electrodes 120 having the tip of the capillary 101 inserted thereinto, the container 201, and the septa 202. The upper opening of the container 201 is sealed by the septa 202. A capillary hole of the septa 202 is provided to each of the capillary electrodes 120. By an auto sampler, the container 201 sealed by the septa 202 is positioned below the load header 115 so that the position of the capillary holes of the septa 202 corresponds to the position of the respective capillary electrodes 120, and then pushed upwardly. As a result, as illustrated in FIG. 5, the hollow capillary electrode 120 and the capillary 101 therein penetrate through the capillary hole of the septa 202, and have the tip part thereof dipped into a solution inside of the container 201. Then, the container 201 is mounted on the lower side of the load header 115 of the oven 106.

At this time, a space is formed between the load header 115 connected to the oven 106 and the septa 202. This is because it is difficult to make the upper part of the container 201 stick to the load header 115 completely because the container 201 is mechanically pushed upwardly from below by the auto sampler. Meanwhile, the space is created also for an intension to provide a space, between the load header 115 and the septa 202, into which an instrument used for pushing down the septa 202 is inserted so as to make its detachment from the capillary electrode 120 easier when the container 201 is brought down so as to be detached from the capillary electrode 120.

However, it has been revealed that, when a space is formed between the load header 115 and the septa 202 and the capillary electrode 120 is exposed, air circulating inside of the device 100 by the cooling fan 119 goes through the space, a difference in heat dissipating effect among capillaries occurs due to the temperature of the air gone through, and a variation of migration time in electrophoresis is observed. This is a phenomenon which has never been observed before.

Figure 6:
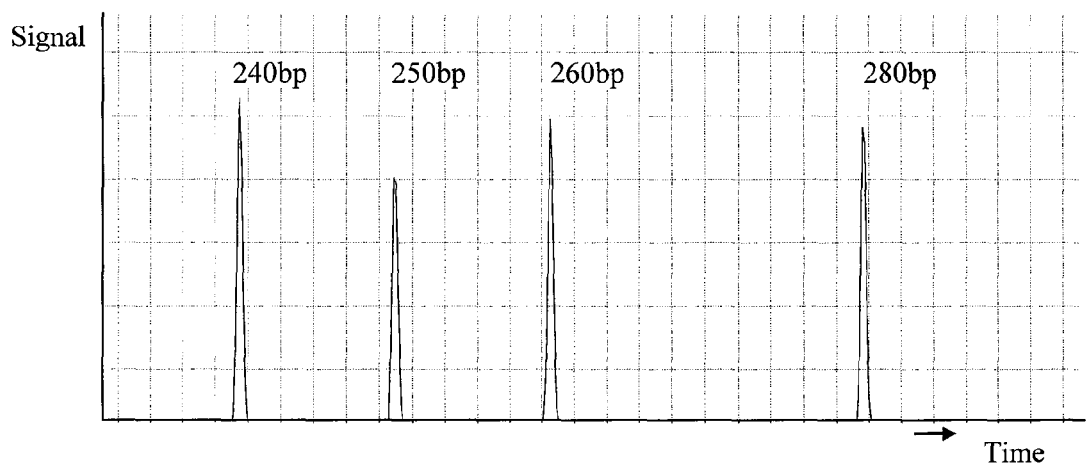
FIG. 6 is a view illustrating an example of a result of migration of DNA fragments.
Figure 7:
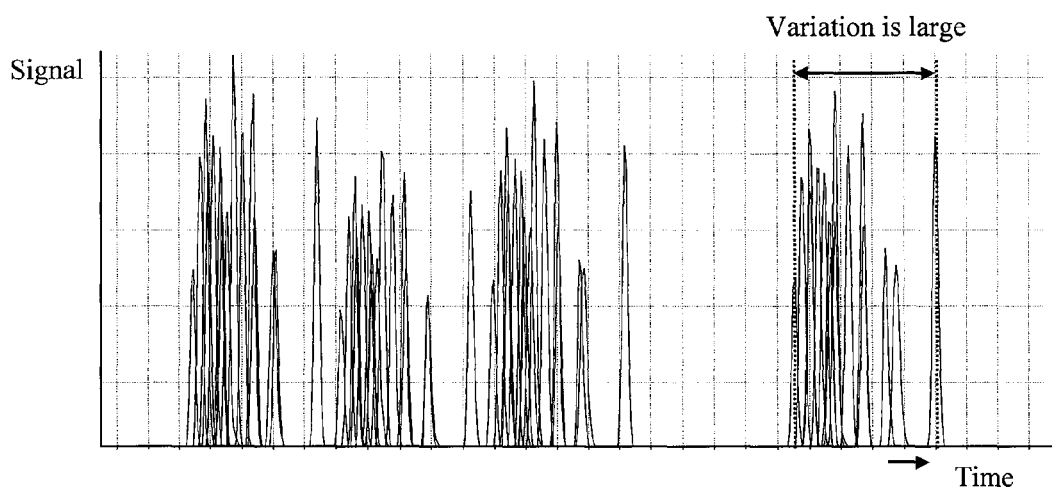
FIG. 7 is a view illustrating superimposed results of electrophoresis with 16 capillaries in the case where the conventional solution holder is used.

FIG. 6 illustrates a measurement example when DNA fragments were subjected to electrophoresis in a device having a structure as illustrated in FIG. 5, and four peaks were detected. FIG. 7 is a view illustrating superimposed results of electrophoresis with 16 capillaries fixed to a single load header 115, and it is observed that the data from 16 capillaries vary in a temporal axis direction.

Based on the problem recognition described above, the present invention is designed with ingenuity so that, between the load header 115 and the container 201, the capillary electrode 120 is not exposed to air circulating inside of the device.

Figure 8A:
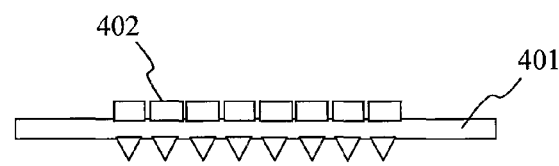
FIGS. 8A and 8B are frame views of a septa according to the present invention.
Figure 8B:
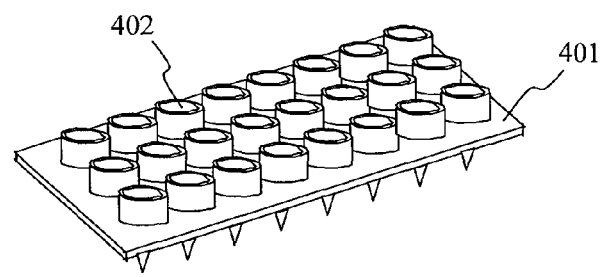

FIGS. 8A and 8B are a frame view of a septa 401 used in an example of the present invention. FIG. 8A is a side view, and FIG. 8B is a perspective view. The septa 401 is provided with multiple cylindrical walls 402 each surrounding a capillary hole through which a capillary (capillary electrode) penetrates. The cylindrical wall 402 is in a state being integrated with the main body of the septa 401, and is composed of a flexible silicone resin having high electric insulation properties.

Figure 9:
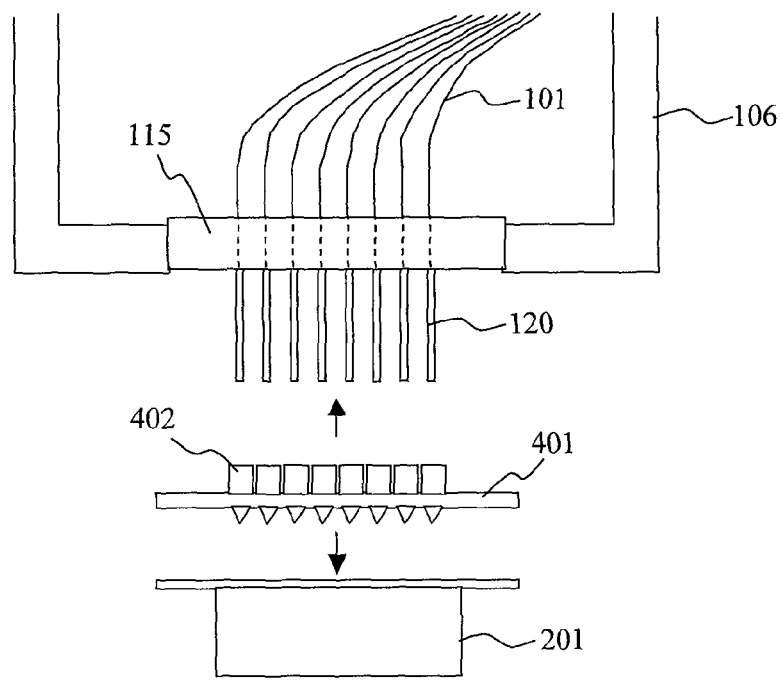
FIG. 9 is a view illustrating the relationship between capillary electrodes and the holder part of the present invention.
Figure 10:
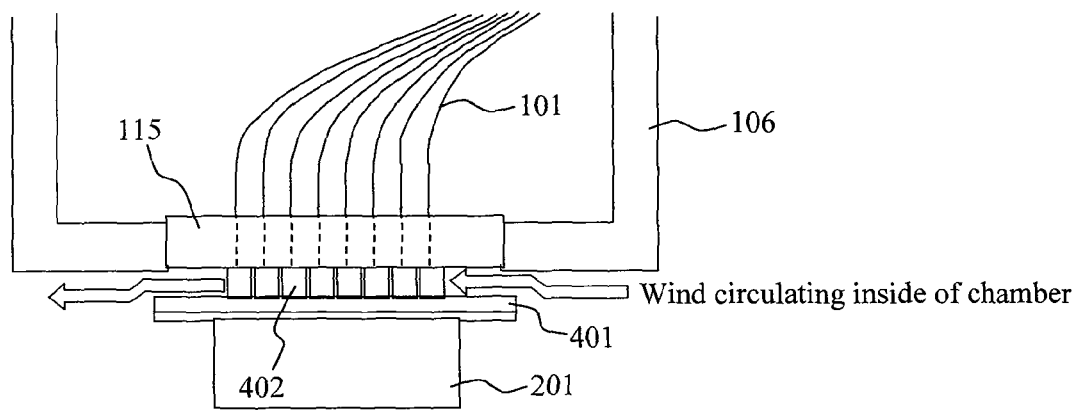
FIG. 10 is a view illustrating the relationship between a septa provided with a cylindrical wall and an oven.

FIG. 9 and FIG. 10 are views each illustrating a holder part of a capillary electrophoresis device to which measures of the present invention are applied. FIG. 9 is a view illustrating the relationship among the capillary electrodes 120 into which tips of the capillaries 101 are inserted, the container 201, and the septa 401. The upper opening of the container 201 is sealed by the septa 401. The capillary hole of the septa 401 and the cylindrical wall 402 surrounding the capillary hole are provided for each of the capillary electrodes 120. By an auto sampler, the container 201 covered with the septa 401 is positioned below the load header 115 so that the position of the capillary holes of the septa 401 corresponds to the position of the respective capillary electrodes 120, and then pushed upwardly. As a result, as illustrated in FIG. 10, the hollow capillary electrodes 120 and the capillaries 101 therein penetrate through the capillary holes each surrounded by the cylindrical walls 402 of the septa 401, and have the tip parts thereof dipped into a solution inside of the container 201, and then the container 201 is mounted on the lower side of the load header 115 of the oven 106.

At this time, a part, which is conventionally exposed in the space between the load header 115 and the septa and exposed to airflow circulating inside of the device, of the capillary electrode is surrounded by the cylindrical wall 402 provided in an upper part of the septa 401, and is blocked from the airflow circulating the device. Accordingly, even if air circulating inside of the device flows into the space between the load header 115 and the septa 401, the air does not directly blow onto the capillaries (capillary electrodes). Therefore, heat dissipation among the capillaries 101 constituting the capillary array 102 is uniform, and the migration time is stabilized.

Figure 11:
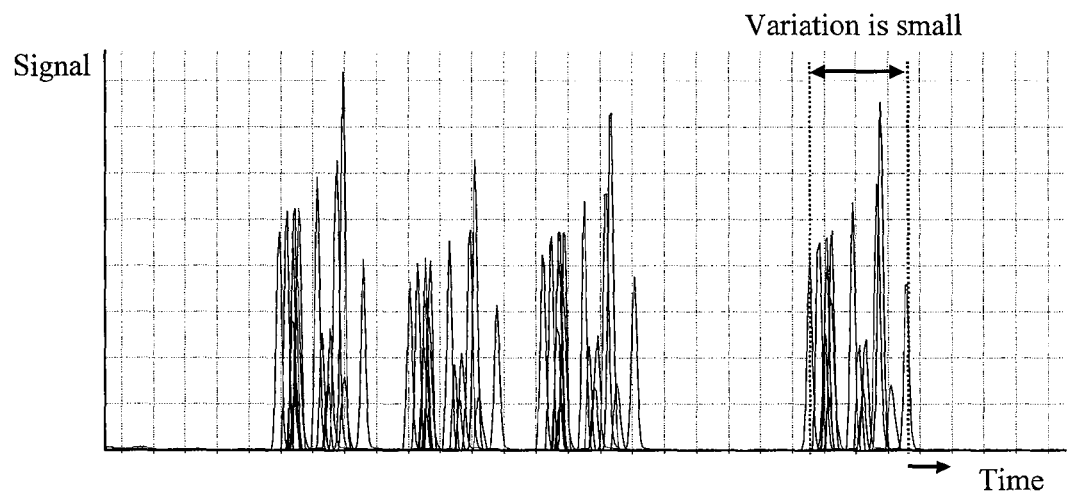
FIG. 11 is a view illustrating superimposed results of electrophoresis with 16 capillaries measured by the device of the present invention.

FIG. 11 is a view illustrating measurement results from when electrophoresis was carried out with 16 capillaries under the same condition as that in FIG. 7, using the capillary electrophoresis device using the septa 401 provided with the cylindrical walls 402. As apprehended from the comparison between FIG. 11 and FIG. 7, by using the septa 401 provided with the cylindrical walls 402, a variation in migration time among capillaries is improved more than before.

Figure 12A:
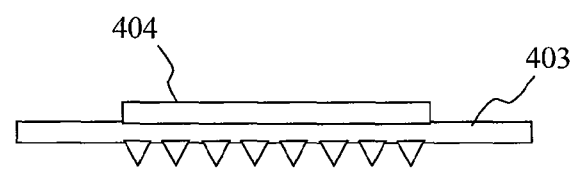
FIGS. 12A and 12B are views illustrating another example of a septa of the present invention.
Figure 12B:
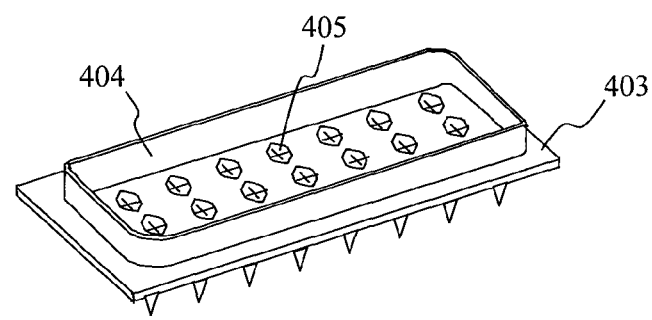

FIGS. 12A and 12B are views each illustrating another example of a septa by the present invention. FIG. 12A is a side view and FIG. 12B is a perspective view. A septa 403 of the present example has a structure in which the whole region provided with multiple capillary holes 405 into which capillaries are to be inserted is surrounded by a cylindrical wall 404. When a container to which the septa 403 of the present example is attached is mounted to the load header 115, the space between the load header 115 and the septa 403 is sealed by the cylindrical wall 404. Accordingly, even if air circulating inside of the device flows into a space between the load header 115 and the septa 404, the air does not directly blow onto the capillaries (capillary electrodes). Therefore, heat dissipation among capillaries constituting a capillary array is uniform; thus, an effect of stabilizing the migration time can be obtained.

EXPLANATION OF REFERENCE NUMERALS

101 . . . capillary
102 . . . capillary array
103 . . . pump mechanism
104 . . . detector
105 . . . high-voltage power source
106 . . . oven
107 . . . auto sampler
108 . . . syringe
109 . . . block
110 . . . check valve
111 . . . polymer container
112 . . . anode buffer container
113 . . . anode electrode
114 . . . cathode electrode
115 . . . load header
117 . . . capillary head
118 . . . capillary cathode electrode
119 . . . cooling fan
120 . . . capillary electrode
201 . . . container
202 . . . septa
205 . . . capillary hole
401 . . . septa
402 . . . cylindrical wall
403 . . . septa
404 . . . cylindrical wall

What is claimed is:

1. A capillary electrophoresis device, comprising:
a capillary;
a power supply that applies a voltage to both ends of the capillary;
an oven that houses a main part of the capillary and maintains an ambient temperature of the main part constant;
a detector that irradiates with an exciting light a sample separated by electrophoresis inside of the capillary and detects fluorescence from the sample;
a load header that is fixed to the oven and has a hollow capillary electrode mounted thereto, a tip part of the capillary being inserted into the capillary electrode;
a holder part in which any one of a sample and an electrolytic solution is held; and
an auto sampler that transfers the holder part, wherein:
the holder part comprises: a container that houses the one of the sample and the electrolytic solution, and has an opening in an upper part thereof; and a septa having a capillary hole through which the capillary electrode projecting from the load header penetrates, the septa covering the upper part opening of the container,
the septa has in an upper part thereof a structure that surrounds the capillary electrode so that air circulating inside of the device does not directly blow onto the capillary electrode, and
the structure that surrounds the capillary electrode is a cylindrical wall that is installed so as to surround a plurality of the capillary holes.

2. The capillary electrophoresis device according to claim 1, wherein the septa is made of a resin material having high electric insulation properties.

\* \* \* \* \*